US010016551B2

(12) United States Patent
Hersenius (10) Patent No.: US 10,016,551 B2
(45) Date of Patent: Jul. 10, 2018

(54) METHOD OF DISPLAYING A PREDICTED STATE, MEDICAL APPARATUS AND COMPUTER PROGRAM (71) Applicant: Gambro Lundia AB, Lund (SE)

(72) Inventor: Patrik Hersenius, Lund (SE)

(73) Assignee: GAMBRO LUNDIA AB, Lund (SE)

(*) Notice: Subject to any disclaimer, the term of this patent is extended or adjusted under 35 U.S.C. 154(b) by 0 days.

(21) Appl. No.: 15/529,604

(22) PCT Filed: Nov. 6, 2015

(86) PCT No.: PCT/EP2015/075926
§ 371 (c)(1),
(2) Date: May 25, 2017

(87) PCT Pub. No.: WO2016/096241
PCT Pub. Date: Jun. 23, 2016

(65) Prior Publication Data
US 2017/0258976 A1    Sep. 14, 2017

(30) Foreign Application Priority Data
Dec. 18, 2014  (SE) .................................. 1451585

(51) Int. Cl.
*A61B 5/00* (2006.01)
*A61M 1/16* (2006.01)
(Continued)

(52) U.S. Cl.
CPC ........ *A61M 1/1615* (2014.02); *A61M 1/1643* (2014.02); *G01F 9/003* (2013.01); *G01F 15/068* (2013.01); *G08B 5/22* (2013.01);
*G16H 40/63* (2018.01); *A61M 2205/15* (2013.01); *A61M 2205/18* (2013.01); *A61M 2205/33* (2013.01); *A61M 2205/3334* (2013.01);
(Continued)

(58) Field of Classification Search
CPC ...................................................... A61B 5/725
USPC .................................................... 340/539.12
See application file for complete search history.

(56) References Cited

U.S. PATENT DOCUMENTS 5,626,140 A     5/1997  Feldman et al.
8,489,408 B2 *  7/2013  Sawanaga .............. G06Q 50/22
                                                          705/2

(Continued)

FOREIGN PATENT DOCUMENTS

WO          0117653      3/2001
WO        2013000777     1/2013

OTHER PUBLICATIONS

Search Report issued in International Patent Application No. PCT/EP2015/075926 dated Feb. 3, 2016.
(Continued)

*Primary Examiner* — Kevin Kim
(74) *Attorney, Agent, or Firm* — K&L Gates LLP (57) ABSTRACT A method of displaying a predicted state of a medical apparatus, and a medical apparatus employing the method are disclosed. The method comprises receiving a sensor signal from a sensor of the medical apparatus, filtering the sensor signal by an adaptive filter such that a predicted signal is achieved, determining a state from the predicted signal, and displaying an indication through a user interface of the medical apparatus based on the determined state.

33 Claims, 8 Drawing Sheets (51) Int. Cl.
  G01F 9/00       (2006.01)
  G01F 15/06      (2006.01)
  G08B 5/22       (2006.01)
  G16H 40/63      (2018.01)

(52) U.S. Cl.
  CPC ............... *A61M 2205/3393* (2013.01); *A61M 2205/505* (2013.01); *A61M 2205/52* (2013.01)

(56) References Cited

U.S. PATENT DOCUMENTS

| | | |
|---|---|---|
| 2002/0111547 A1 | 8/2002 | Knobbe et al. |
| 2003/0128125 A1 | 7/2003 | Burbank et al. |
| 2003/0216888 A1* | 11/2003 | Ridolfo .............. G05B 23/0283 702/181 |
| 2004/0039243 A1 | 2/2004 | Teixeira |
| 2012/0283581 A1 | 11/2012 | Olde et al. |
| 2013/0060480 A1 | 3/2013 | Korhonen et al. |
| 2013/0150766 A1 | 6/2013 | Olde et al. |
| 2013/0231543 A1 | 9/2013 | Facchinetti et al. |
| 2014/0231319 A1 | 8/2014 | Olde et al. |

OTHER PUBLICATIONS

Written Opinion issued in International Patent Application No. PCT/EP2015/075926 dated Feb. 3, 2016.

* cited by examiner

METHOD OF DISPLAYING A PREDICTED STATE, MEDICAL APPARATUS AND COMPUTER PROGRAM

PRIORITY CLAIM

The present application is a National Phase of International Application No. PCT/EP2015/075926, filed Nov. 6, 2015, which claims priority to Swedish Patent Application No. 1451585-2, filed Dec. 18, 2014, the entire contents of each of which are incorporated herein by reference and relied upon.

TECHNICAL FIELD

The present invention generally relates to a method of displaying a predicted state of a medical apparatus, such a medical apparatus and a computer program for implementing the method.

BACKGROUND

Monitoring of proper operation of medical apparatuses is desired. Therefore, it is desired that physicians and other personnel operating the medical apparatus should be supported by the medical apparatus to be able to provide proper operation of the medical apparatus, especially when processes, such as treatments, may last for a long time. For example, at dialysis treatments, the operator may be operating several dialysis machines, or may also operate other medical equipment at the same time as operating the dialysis machine, such as for example in acute medicine. An example of this is alarm functions that are implemented in medical apparatuses to clearly indicate if a critical state has occurred. However, it is of course best if the apparatus may be operated such that a critical state never occurs or at least is avoided as much as possible. Considering the example of a dialysis machine again, the difference in some parameters between normal operation and a critical state may be very little particularly for low-weight patients, where children are typically represented. In this and similar examples, there is a desire to provide adequate support to the operator such that the medical apparatus may be operated avoiding reaching a critical state as much as possible.

SUMMARY

An object of the invention is to at least alleviate the above stated problem. The present invention is based on the understanding that there may be very little difference between sensor signals at normal operation and at malfunction, e.g. a very low flow (or distributed volume over time) prescribed to light weight patients, and a situation where the flow is low depending on malfunctions in the hydraulic system for delivering the fluid. Additionally or alternatively, the sensor signal may be noisy, e.g. due to mechanical disturbances to e.g. scales. The inventor has found that by a combination of signal processing of the sensor signal and provision of a status indicator of how well/bad the prescription is followed to an operator of the machine may help the operator to decrease the amount of critical situations and thus alarms.

According to a first aspect, there is provided a method of displaying a predicted state of a medical apparatus. The method comprises receiving, continuously or repeatedly during operation of the medical apparatus, a sensor signal from a sensor of the medical apparatus, filtering the sensor signal by an adaptive filter such that a predicted signal is achieved, determining a state from the predicted signal, and displaying an indication through a user interface of the medical apparatus based on the determined state.

The filtering may be made by a Kalman filter.

The filtering may further be made by, in addition to the adaptive filter, a controller, preferably a proportional-integral (PI) controller. The filtering may further, by the controller, provide a signal for controlling a function of the medical apparatus being associated with the sensor.

The sensor may comprise a flow sensor, wherein the method may comprise determining a flow by the flow sensor.

The sensor may comprise scales. The method may comprise determining a flow based on difference in weight measured by the scales from the predicted signal.

The method may comprise estimating an error based on a set-point corresponding to the determined flow, wherein the determining of the state is based on the estimated error.

The state may be one of at least two non-critical states and a critical state. An alarm may be activated when the critical state occurs.

The displaying of the indication may comprise a thermometer or traffic light illustration of the determined state.

The indication may comprise a meter indication.

The indication of the state may comprise an indicator on at least one of:

how well the state of the operation of the medical apparatus corresponds to prescribed operation; and how much the state of the operation of the medical apparatus deviates from prescribed operation.

The method may further comprise estimating, by the filtering, a noise level of the sensor signal, wherein the displaying of the indication may comprise a noise level indicator.

Interactions with the medical apparatus known to introduce false error conditions may be taken into account by the adaptive filter. Examples on such interactions may be change of containers and/or consumables, moving the medical apparatus, etc. The sensor may comprise scales monitoring weight of a container holding medical fluid to be consumed during operation of the medical apparatus, and the interactions known to introduce false error conditions may comprise replacing the container.

The method may comprise receiving and filtering a plurality of sensor signals, and respective states may be determined, wherein the respective states may be displayed.

The method may further comprise receiving, continuously or repeatedly during operation of the medical apparatus, at least one further sensor signal from a further sensor of the medical apparatus, filtering the at least one further sensor signal by a respective adaptive filter such that respective predicted error signals are achieved, determining a respective state from the respective predicted error signal, and displaying a respective indication based on the respective determined state. The method may comprise estimating an aggregate noise state based on the filtering of the respective sensor signals, and displaying an indicator of the aggregate noise state.

According to a second aspect, there is provided a medical apparatus comprising a sensor arranged to provide a sensor signal, continuously or repeatedly during operation of the medical apparatus, for a function of the medical apparatus, an adaptive filter arranged to filter the sensor signal such that a predicted signal is achieved, a state determinator arranged to determine a state from the predicted signal, and a user interface arranged to display an indication based on the determined state.

The adaptive filter may be a Kalman filter.

The apparatus may further comprise a controller, preferably a proportional-integral (PI) controller, arranged to provide a signal for controlling the function of the medical apparatus being associated with the sensor.

The sensor may comprise a flow sensor arranged to determine a flow.

The sensor may comprise scales. The flow may be determined based on difference in weight measured by the scales from the predicted signal.

The apparatus may be arranged such that an error is estimated based on a set-point corresponding to the determined flow, wherein the state determinator may be arranged to determine the state based on the estimated error.

The state may be one of at least two non-critical states and a critical state. The apparatus may comprise an alarm mechanism which is activated when the critical state occurs.

The user interface may be arranged to display the indication as a thermometer or traffic light illustration of the determined state.

The user interface may be arranged to display the indication as a meter indication.

The indication of the state may comprise an indicator on at least one of:

how well the state of the operation of the medical apparatus corresponds to prescribed operation; and how much the state of the operation of the medical apparatus deviates from prescribed operation.

The adaptive filter may further be arranged to estimate a noise level of the sensor signal, and the user interface may be arranged to display a noise level indicator.

According to a third aspect, there is provided a computer program, for a processor of a medical apparatus, comprising computer program code including computer executable instructions, which when downloaded and executed by the processor of the medical apparatus causes the medical apparatus to perform the method of the first aspect.

Other objectives, features and advantages of the present invention will appear from the following detailed disclosure, from the attached dependent claims as well as from the drawings. Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings.

DETAILED DESCRIPTION

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on an embodiment of the present invention applicable to a machine for extracorporeal blood treatment and in particular to a dialysis machine or monitor. However, it will be appreciated that the invention is not limited to this application but may be applied to many other medical devices including for example infusion pumps, peristaltic pumps, liver treatment devices, or ultra filtration devices, and also for plasma replacement, extracorporeal lung support such as carbon dioxide removal, etc. Thus, the benefits may be found both in dialysis care and within other treatments for supporting body functions, e.g. at trauma care, more or less complicated surgical treatment, critical infections, etc. For enabling better understanding of this disclosure, a medical apparatus of a type particularly suitable for the invention will be given with greater detail with reference to FIG. 1, wherein a person skilled in the art readily will understand analogous application to other medical apparatuses where the similar effects are desired. Thus, the apparatus demonstrated with reference to FIG. 1 should be considered as one example of a suitable medical apparatus, but the type of machine and its details should not be considered to limit the application of the teachings herein only to that particular machine. Contrary, the effect of predicting state of a medical apparatus is in principle desired in any medical apparatus where monitoring of one or more functions of the apparatus is to be performed.

Machine Parts

Figure 1:
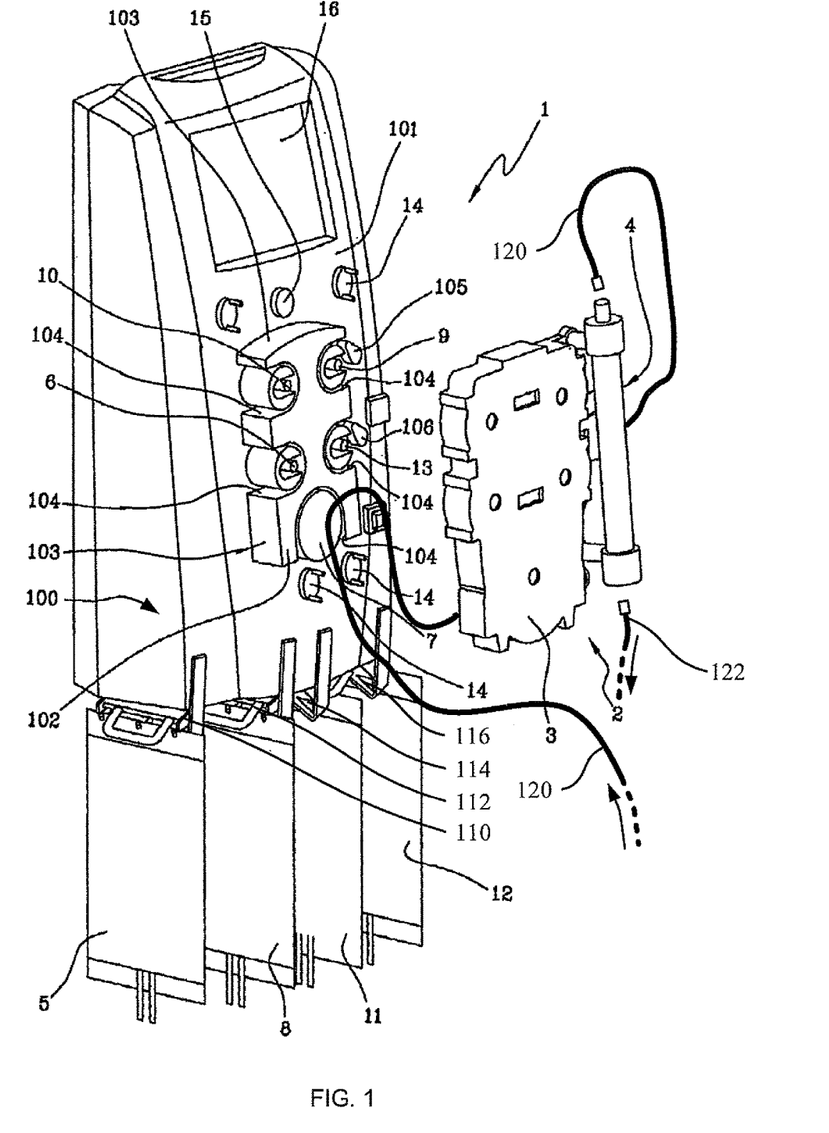
FIG. 1 illustrates an embodiment according to an example of a machine.
Figure 2:
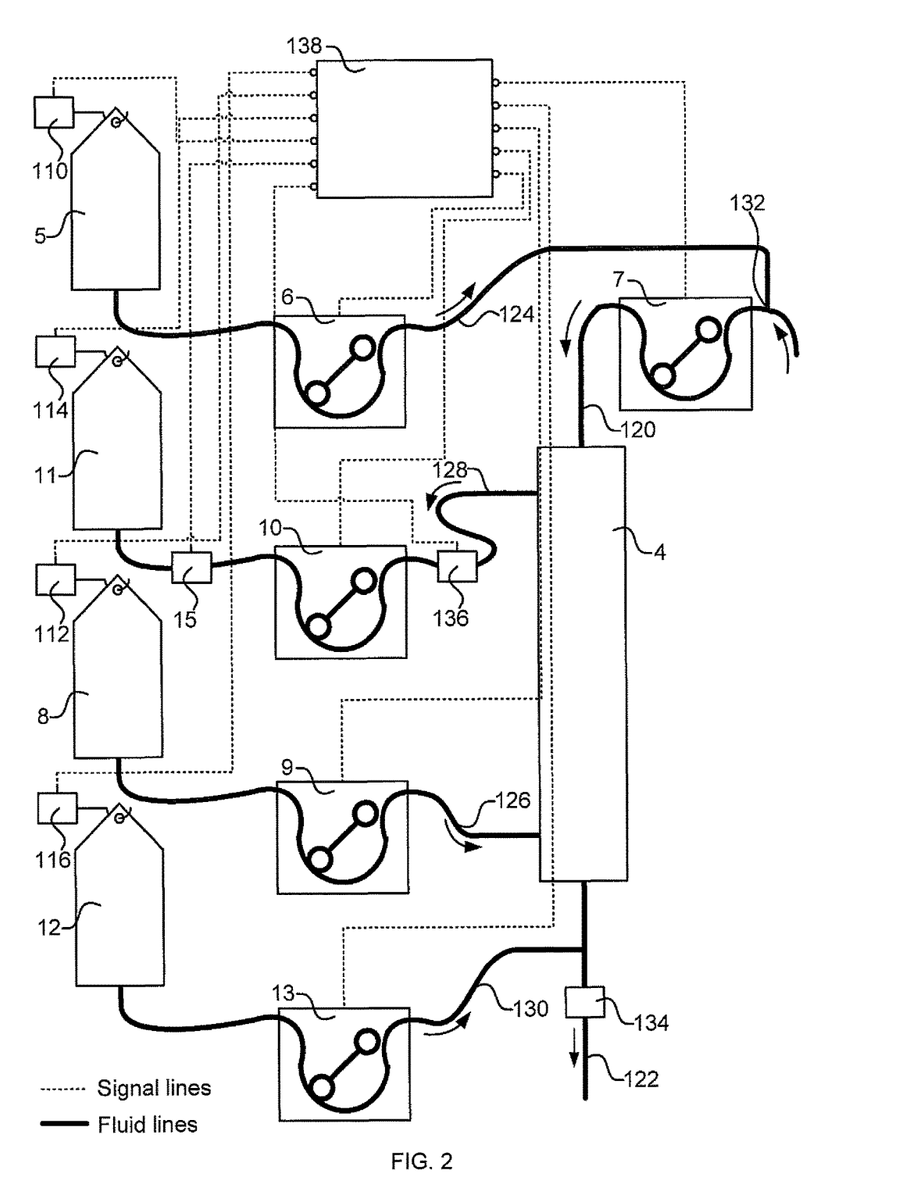
FIG. 2 is a block diagram schematically illustrating functional parts of the example of the machine of FIG. 1.

FIG. 1 illustrates an embodiment according to an example of a machine 1, where a machine 1 for extracorporeal blood treatment is represented in the illustrated embodiment by a dialysis machine which is suitable for continuous treatment of acute kidney failure. FIG. 2 is a block diagram schematically illustrating functional parts of the machine 1 of FIG. 1, and the same reference numerals are used in FIGS. 1 and 2 where illustrated in both the figures. It is to be noted that FIG. 2 shows some elements that are not visible or illustrated in FIG. 1, and some elements from FIG. 1 are omitted in FIG. 2, for the sake of easier understanding, where their presence is not necessary for the explaining of the function of the machine 1. An integrated module 2 may be coupled to the dialysis machine 1. The integrated module 2 may be constituted by a combination of at least one support element 3 of a distribution circuit (of known type and not illustrated) arranged on the support element 3, and a blood treatment unit 4. The blood treatment unit 4 may be, for example, a plasma filter, a hemodialysis filter, a hemofiltration filter, or a different unit.

The hydraulic circuit, which is completed by a combination of the integrated module 2 and the machine 1, comprises a blood circuit which removes blood from a patient, for example via a catheter inserted in a vascular access of the patient, and takes the blood through a blood removal line 120 to the treatment unit 4.

The blood passes through a first chamber (blood chamber) of the treatment unit 4 and, via a return line 122, and is transported back to the patient.

Downstream of the blood removal zone, connection is made between the removal line 120 and an auxiliary pre-infusion line 124.

In particular, the machine may include at least one container 5 of a first sterile fluid for supplying the pre-infusion line; fluid transport means, in the embodiment constituted by a pre-infusion pump 6, for example a peristaltic pump, control the flow of fluid in the pre-infusion line 124 directly into the blood via a direct connection 132 to the blood removal line 120, and may therefore also be referred to as pre-blood pump 6.

Generally the container 5 of the first sterile fluid may contain a pre-infusion fluid, although the same container 5 may be used for containing an anticoagulant, usually of a locally-acting type such as citrate.

The machine 1 further comprises means for transporting fluid, i.e. in the embodiment at least one blood pump 7 for control and management of a correct blood flow in the circuit. The blood pump 7 is peristaltic.

After passing the first blood chamber of the treatment unit 4, where substance-exchange and molecular and fluid exchange takes place through a semi-permeable membrane, the treated blood enters the return line 122, passing a gas separator 134 (generally air), where any air bubbles present in, or introduced to, the blood during treatment are expelled.

The distribution circuitry may comprise a first circuit of a second sterile fluid (dialyzing liquid) having at least one inlet line 126 to the blood treatment unit 4 and an outlet line 128 from the treatment unit 4.

At least one container 8 of the second sterile fluid, e.g. dialysis fluid, may be destined to supply the inlet line 126 of the first circuit.

The inlet line 126 may be destined to cooperate with means for fluid transport, being at least one pump 9 (in the embodiment a peristaltic pump, e.g. dialysis fluid pump 9) predisposed on the frontal part of the machine 1 to control the flow of the second sterile fluid coming from the container 8, and to define a circulation direction.

The second sterile fluid (e.g. dialysis fluid) passes the inlet line 126 and enters the second chamber (dialysis side) of the blood treatment unit 4.

In particular the first chamber (blood chamber), passed by the blood flow, is separated from the second chamber (dialysis chamber), passed by the second sterile fluid, by a semi-permeable membrane which enables passage of the damaging molecules and substances and fluids in the blood towards the second sterile fluid (dialysis fluid), mainly through convection and diffusion processes; at the same time, and by the same principles, passage of substances and molecules from the second sterile fluid and towards the blood is allowed.

The used fluid, for dialysis, enters the outlet line 128 of the first circuit and passes a pressure sensor 136 for controlling the functioning of the line 128. Means for transporting the fluid, for example an effluent drainage pump 10, are present, which control the flow in the fluid circuit outlet line. This pump 10, as the others, may be peristaltic.

The discharge fluid then passes a blood leak detector 15 and is sent on to an effluent collection container 11.

An infusion line 130 is located on the return line 122 of the blood circuit. In particular, a third sterile fluid (infusion fluid) is sourced from at least one auxiliary container 12 and, by action of a fluid transport means, generally an infusion pump 13 which controls flow (in the embodiment a peristaltic pump), is sent directly to the blood circuit return line 122.

The machine 1 is provided with means for determining at least the weight of the container 5 of the first sterile fluid and/or the container 8 of the second sterile fluid and/or the container 12 of the third sterile fluid and/or the discharge container 11, and/or the flows from/to the containers 5, 8, 11, 12. The means for determining may be constituted by weight sensors, for example scales 110, 112, 114, 116, which may be independent scales for each container or fluid bag associated to the machine, or flow sensors such as ultrasonic, coriolis, pressure gradient, etc. flow sensors measuring volumetric or mass flow.

There may be, as in the illustrated example, at least four of these scales 110, 112, 114, 116 present, each independent of the others, and each predisposed to measure the respective weight of a container 5, 8, 11, 12. More or fewer scales and corresponding containers are also possible, and the number is determined from the type and use of the machine. The signals associated with these scales 110, 112, 114, 116 will be particularly elucidated below since they may be prone to noise caused by both noise present in connection with all electrical and electronic equipment, and noise introduced by the environment which may have impact on the exposed position of the containers 5, 8, 11, 12 and the machine 1 as a whole. Other types of sensors for determining flow, as discussed above, may substitute or add to the scales. For simplicity of understanding the principles, the example using scales will be used in the rest of this disclosure not to obstruct the gist of the invention, but it should be kept in mind that the other examples of flow sensors are equally feasible for the examples given below.

There is also a central processing unit, CPU, 138 which is active on the blood circuit, for example on the blood pump 7 and the bubble sensor 134. The CPU 138 may also be involved in controlling other parts of the machine 1, such as for example a user interface, communication interfaces, etc., and the CPU may comprise one or more processors performing different tasks or performing tasks in parallel, i.e. for enhancing secure operation. The user interface may comprise a screen 16, for example a touch screen, for interaction with a user. The CPU 138 is also used for controlling the first circuit of the second sterile fluid, and in particular to receive data sent by the scales 112 relating to the weight of the container 8; it is also active on the pump 9, the pressure sensor 136, the drainage pump 10 and the scales 114 weighing the effluent discharge container 11. The CPU 138 is also active on the infusion line 130 of the third sterile fluid, monitoring the weight of the container 12 (measured by scales 116), and also controls the infusion pump 13. Finally, the CPU 138 is active on the auxiliary line for pre-infusion of the first sterile fluid, measuring the weight of the container 5 via scales 110 and commanding the pre-infusion pump 6 according to the treatment to be carried out.

The above, purely descriptive, account of the hydraulic circuitry of the example of the machine 1 for extracorporeal blood treatment will now be followed by a brief explanation of how the device functions.

Before the actual treatment begins, the apparatus is prepared. The whole hydraulic circuitry and the treatment unit are correctly associated to the machine so that the various peristaltic pumps engage the respective tracts of tubing, and all the sensors are correctly positioned; also, the relative bags containing the various fluids are joined up to the respective supply or receiving lines of the liquids, and the blood circuit is connected up to an artery or vein of the patient. When set-up is complete, an initial circulation of the blood internally of the respective circuit may be made.

According to the type of treatment selected (pure ultrafiltration, hemodialysis, hemofiltration, hemodiafiltration, etc.), the machine 1 for extracorporeal blood treatment is automatically activated and controlled by the processing unit 138.

The machine 1 exhibits a machine body 100 provided, on a front surface 101 thereof, with peristaltic pumps 6, 7, 9, 10, 13, destined to cooperate in use with respective tracts of e.g. U-shaped tubing 120, 124, 126, 128, 130 on the integrated module 2. Other types of pumps and thus corresponding connections of tubing are also feasible, although the peristaltic pumps provide for example the benefit of provision of sterile tubing sets to be applied where the mechanics of the pump does not come into direct contact with the fluids.

The machine body 100 exhibits a relief acting as a positioning guide 102 which projects from the front surface 101, which is complementarily shaped with respect to the support element 3 with which it will couple in use.

In other words, the guide 102 exhibits a lateral surface 103 which, when the integrated module is coupled thereto, is contained within a perimeter wall of the support element 3.

The peristaltic pumps also project from the front surface 101 of the machine body 100 and at least a part of the lateral surface of the pumps is complementarily shaped with respect to the perimeter wall of the support element 3.

The projecting peristaltic pumps and the guide 102 in combination may define seatings 104 having a semicircular shape, i.e. a U-shape, which seatings 104 are destined to receive the corresponding tracts of U-shaped tubing 120, 124, 126, 128, 130 of the circuitry.

A first mobile element 105 and a second mobile element 106, substantially identical and borne directly on the machine body 100, may be destined to be active on the infusion and/or inlet line 126 of the second sterile fluid (the first mobile element 105) and, respectively, on the pre-infusion line 124 and/or the post-infusion line 130 of the third sterile fluid (the second mobile element 106). In particular the mobile elements 105, 106 may be controlled by the CPU 138 to selectively allow or block passage of fluid into one or another of the lines.

The front surface of the machine 1 may further exhibit a plurality of fastening elements 14 for fixing the pressure sensors; the pressure sensors associated to the circuitry of the integrated module may be connected to the CPU 138.

The blood leak detector 15 may also be predisposed on the front surface of the machine, and during the apparatus preparation process is associated to the fluid circuit outlet line 128 from the treatment unit 4.

Monitoring of signals is as demonstrated above important to determine if any value should reach a critical amount. This may become a more difficult task when the signals reach the boundaries of normal operation. One such example is delivering small amounts of fluid, e.g. to light-weight patients such as children. This is particularly the case if the sensors to deliver the signals are inherently prone to noise. Then it may become hard to discriminate anomalies in the signal from the noise.

The example on a medical machine above is based on containers 5, 8, 11, 12 for fluids, and they are illustrated as bags. The use of bags has shown to be a beneficial way of handling sterile solutions and also for handling effluent fluids such that impurities and infections are kept under control. However, other types of containers are also possible, such as a bottle or canister which are adapted for use with the medical machine. Further types of containers may be used applying the principles of this disclosure, although the containers may not be the designated for the machine or particularly adapted to for example the scales of the machine. In such cases, the use of flow meters may be preferable. The use of solutions provided through so called on-line set-ups, i.e. one or more of the fluids being centrally provided over a hydraulic network at a hospital or clinic, to medical machines may be a feasible alternative, wherein flow needs to be determined by flow sensors. Considering the illustration of FIG. 1, one or more of the containers 5, 8, 11, 12 would in an on-line set-up be substituted by a connection to an on-line fluid port providing or evacuating the fluid in question. The on-line set-ups may be preferred where large quantities of solutions are handled.

Operation

Figure 3:
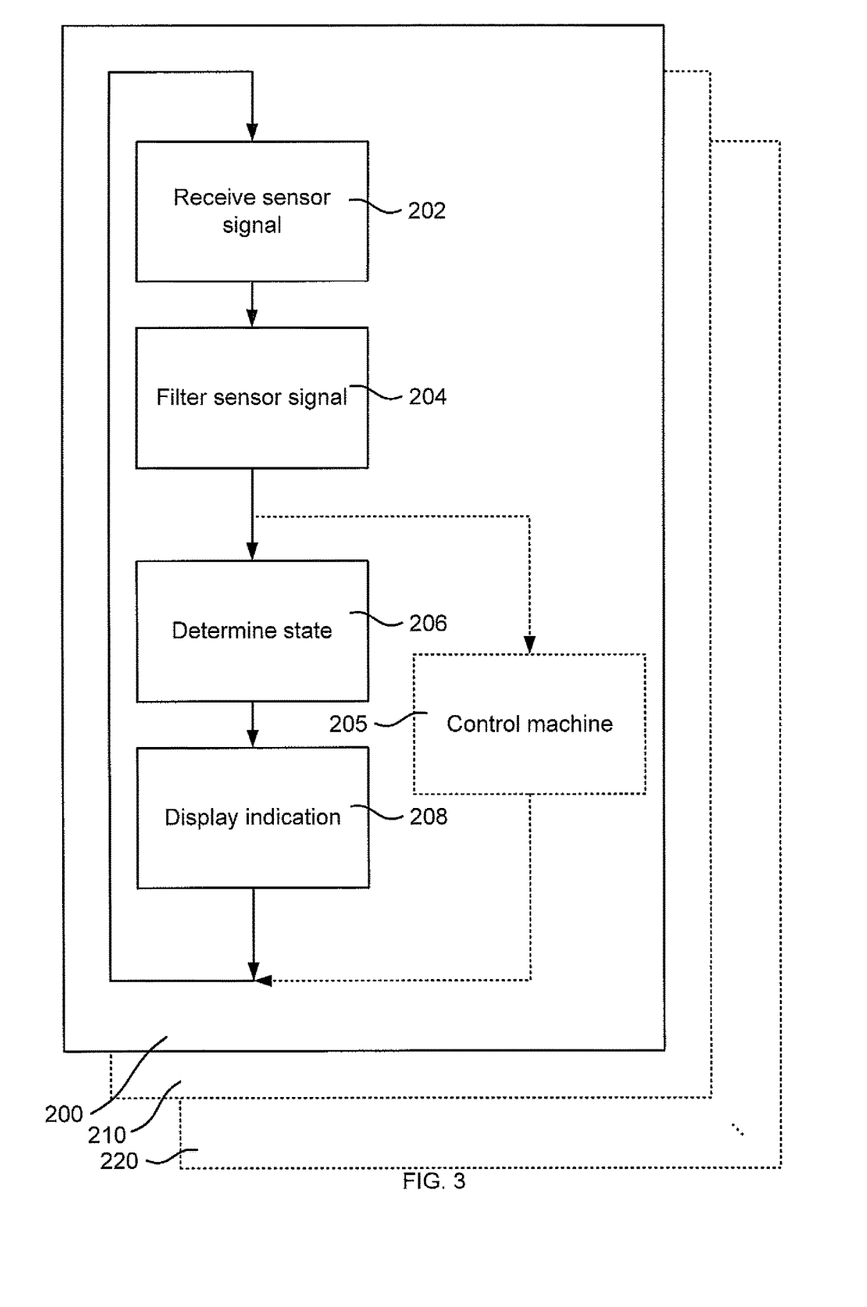
FIG. 3 is a flow chart schematically illustrating a method according to an embodiment.

FIG. 3 is a flow chart schematically illustrating a method 200 according to an embodiment of displaying a predicted state of a medical apparatus. The method comprises receiving 202, continuously or repeatedly during operation of the medical apparatus, a sensor signal from a sensor of the medical apparatus. For example, the sensor may be one of the scales 110, 112, 114, 116 demonstrated above, wherein a flow may be determined based on difference in weight measured by the scales, based on the weight-volume relation of the fluid in case of prescription being volume based. Thus, flow from/to one of the bags 5, 8, 11, 12 may be determined. The flow or, seen over time, delivered volume may be prescribed for a particular patient. Mutatis mutandis, the weight and change in weight (mass flow) may be used directly for prescription and control, and are therefore completely interchangeable with the demonstrations below which refer to volume and flow. As will be demonstrated below, particularly for light weight patients such as children, there may be very little difference between a very low flow (or distributed volume over time) e.g. prescribed to light weight patients, and a situation where the flow is low depending on malfunctions in the hydraulic system for delivering the fluid. In addition to this, the sensor signal may be noisy, e.g. due to mechanical disturbances to the scales. Issues may also occur for more "normal" flow rates when the sensor signal becomes very noisy, e.g. because of the medical apparatus being exposed to mechanical interference such as movements or vibrations. To better discriminate between an acceptable deviation from the prescribed low flow, as seen by the sensor, and malfunction of the hydraulic system, e.g. kinked lines etc., as also seen by the sensor, the sensor signal is filtered 204 by an adaptive filter. The adaptive filter is arranged to provide a predicted error signal, wherein issues of lag and noise are alleviated. The adaptive filter may for example be a Kalman filter, as will be further elucidated below. A state is determined 206 from the predicted error signal. Thus, the state may be given from a prediction of deviation between the measured amount and the prescribed amount. The states may be one or more non-critical states and a critical state. An alarm may be activated when the critical state occurs. The determined state is displayed 208 as an indication based on the determined state. The non-critical state or states however indicates to an operator the condition, e.g. how well the state of the operation of the medical apparatus corresponds to prescribed operation and/or how much the state of the operation of the medical apparatus deviates from prescribed operation. The operator may thus take any suitable action, if found necessary from the indicated non-critical state such that the critical state, and corresponding alarm, may be avoided. It is beneficial if the indication of the state is readily noticed by the operator, e.g. by a quick glance at a display of the medical apparatus. The indicator may for example comprise a thermometer or traffic light illustration of the determined state. Thus, the thermometer illustration may, as discussed above, illustrate how well the state of the operation of the medical apparatus corresponds to prescribed operation and/or how much the state of the operation of the medical apparatus deviates from prescribed operation, wherein a state corresponding to one end of the thermometer illustration corresponds to the critical state. The traffic light illustration may for example illustrate good correspondence to prescribed operation, i.e. the estimated deviation therefrom is low, when indicating green, while yellow may indicate deviations therefrom, however non-critical, and red may indicate that a critical state is reached or imminent. Other alternatives of indications are also possible, and the choice of indication may follow other graphical user interface items of the medical apparatus such that the operator readily recognises the information intended to be provided. The indication may for example comprise a meter indication, characters, numbers and/or symbols, change of appearance of the screen, etc, as or in combination with the examples given by FIGS. 8 to 19.

The filtering may further comprise estimating a noise level of the sensor signal. The noise level may for example be estimated as a deviation based on the unfiltered signal and the filtered signal, e.g. observed in a time window, or by any known way of determining or estimating deviation or variation. A noise level indicator may be included in the displayed indication. Some of the interactions with the medical apparatus are known to introduce false error conditions, e.g. change of bags, checking of connections to bags, etc. in the example above. These conditions may be taken into account by the adaptive filter. For example, a model applied by the adaptive filter may be adapted to discriminate such interactions from other events. Other conditions may be hard to have any influence on by the operator. An example is a clinic aboard a ship where the conditions at sea, engine conditions, other operations performed on the ship (loading/unloading, launching of airplanes, firing), etc. causing the ship to move or vibrate may imply mechanically introduced noise to scales. The operator may then see, on the indication on noise level that proper sensor signals cannot be acquired, and maybe decide to postpone at least that part of the treatment until conditions become better since alarm situations are likely to occur too frequently because of the noisy signal, and patient safety may not be safeguarded (see e.g. below about the signal also being used for controlling the medical apparatus).

The filtered signal may be used as a signal for controlling 205 a function of the medical apparatus being associated with the sensor. For example, the filtering 204, in addition to the adaptive filter, may further comprise a controller, e.g. a proportional-integrating (PI) controller, providing a control signal for a part of the medical apparatus. Or seen the other way around, the control signal may be used for the state determination 206.

An example of a medical apparatus is demonstrated above with reference to FIGS. 1 and 2. Other examples are infusion pumps and other medical apparatuses including infusion where a sensor signal, which provides a signal for monitoring that a subscription is followed and/or controlling accordingly, may be prone to noise, in particular introduced by mechanical surroundings.

Further similar methods 210, 220 operating with other sensors and/or other amounts, may be performed in parallel, and may be more or less independent or may share some information, e.g. information for model update etc. in operation.

The adaptive filtering may be based on an approach where a part of the filter makes a prediction based on a model while another part of the filter performs an update of the model, which is used by the prediction part for next prediction, etc. One type of filters employing this approach is Kalman filters. Briefly explained, the prediction part makes a state estimate, i.e. an estimation of the state variable or variables, and also makes a covariance estimate. A predicted measurement estimate may thus be formed. These predictions are performed based on a model and present values. The update part determines the corresponding estimate, however not predicted, and checks with previous estimate given by the prediction part. This gives a so-called innovation process or variable, which is the difference between prediction and actual measurement, wherein a corrected state estimate may be provided using a filter gain employed on the innovation variable. The next predicted state estimate may be provided as a function, based on the model, of the corrected state estimate and the measured input value.

In addition to the noisy character of the input signal from e.g. the scales, the sensor value may also provide a certain lag due to inherent characteristics of the scales, e.g. based on the sensor value being filtered as a mean value of a number of measurements before being provided at an output of the sensor. The adaptive filter may also take care of that issue if included in the model of the adaptive filter.

Consider an example where an input action affects the system, e.g. rotation of a fluid pump head creating a force that drives fluid towards or from a fluid container. Scales measure the weight of the container, and the measurement signal is provided to an adaptive filter and then to a controller for the fluid pump. The adaptive filter is used to compensate for time delays and smooth noisy signals from the scales. A model of how the pump flow into or from the container translates into scales readings of the container weight is provided in the adaptive filter. A mathematical model of the system, i.e. fluid container and scales dynamics, is thus formed. For a Kalman filter, a predicted state estimate is made for the real system, a predicted estimate covariance matrix is used for telling how trustworthy the predicted state estimate is, and the filter is updated accordingly. The update is made by observing an actual state of the system and a measurement residual and its covariance are calculated. The estimate is updated based thereon and the predicted covariance matrix is calculated for the updated estimate, and a new prediction is made using the updated model. That is, the model and the real system are checked against each other for each measurement, and the model is updated accordingly such that a fairly good prediction of weight estimate may be made. The filter output is fed to the controller, i.e. the estimate of the actual container weight at a particular time, where it is compared, e.g. by a subtraction operation to generate a deviation, with a set point value representing a prescribed value, such that the controller is able to provide a control output for driving the pump. The benefits of the adaptive filter are illustrated with reference to FIGS. 3 and 4, where comparisons with a non-adaptive filter (low-noise filter) are also made.

Figure 4:
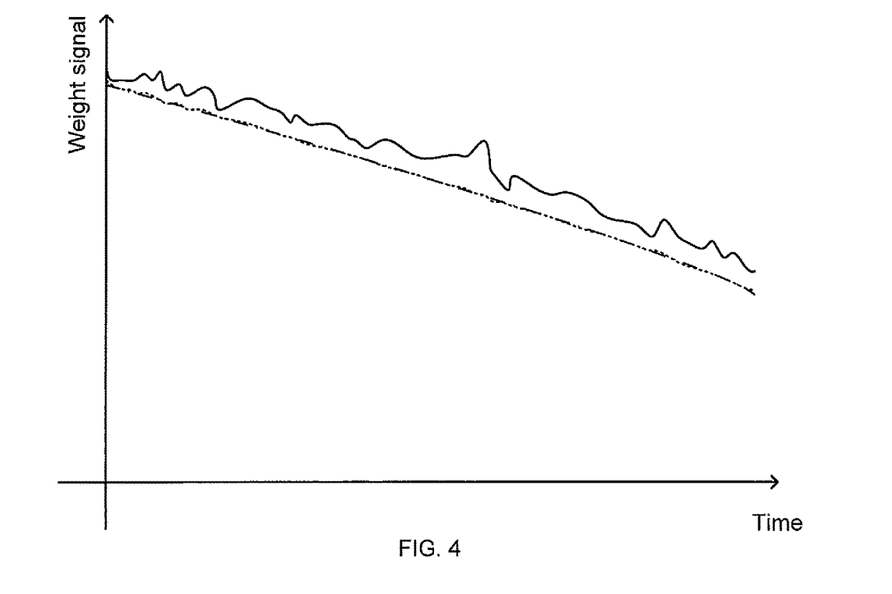
FIGS. 4 and 5 are signal diagrams.
Figure 5:
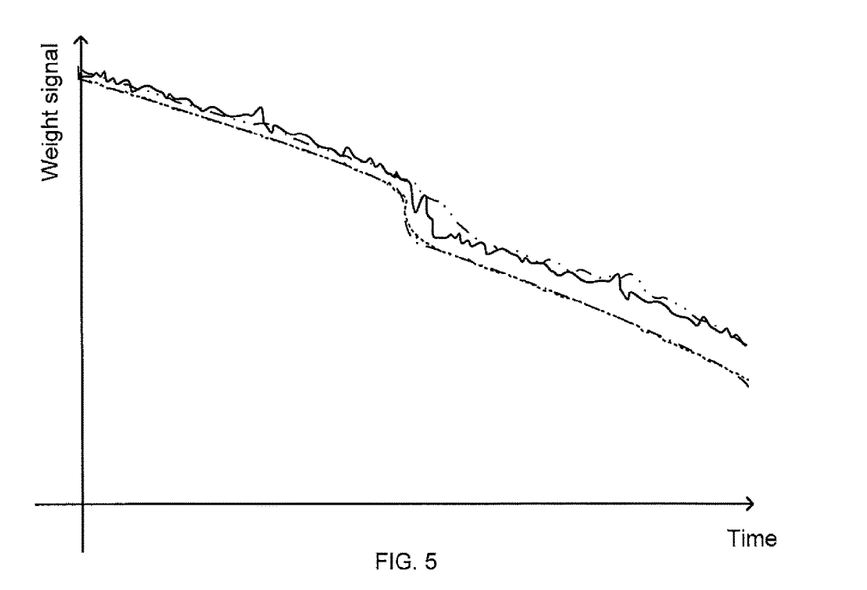

FIG. 4 illustrates an example of such a sensor signal (solid line), the sensor signal filtered by the adaptive filter (hashed line), and a theoretical correct value (dot-dash line). The noisy characteristic of the sensor signal can be seen from the variations between samples and the lag can be seen by the offset from the theoretically correct line. The (theoretical) sensor curve in the example is smooth, which may be an example where flow works fairly well according to a prescription, and for that type of curve a rather simple low-pass filter would have worked too. For an application where flow is considered, i.e. difference between two instances of the signal, the lag would be cancelled if the lag was constant. However, a low-pass filter inherently introduces a lag in itself, and if the theoretically correct value provides a leap, that anomaly would be recognised late depending on both the lag of the sensor signal and the lag of the low-pass filter. The signal provided from the adaptive filter would show that anomaly with significantly less lag, and would thus provide possibility to show an indication thereon, as discussed above, at an earlier stage such that an operator would be given the possibility to react on the situation. An example is given in FIG. 5, where it is illustrated a sensor signal (solid line), the sensor signal filtered by the adaptive filter (hashed line), and a theoretical correct value (dot-dash line). Further, a low-pass filtered signal (double-dot-dash line) is illustrated for comparative purposes. Here, it can be seen that the anomaly would be hard to discriminate from normal operation (as illustrated in FIG. 4) while the signal filtered by the adaptive filter would provide a fairly true image of the correct signal and with considerably less lag.

Figure 6:
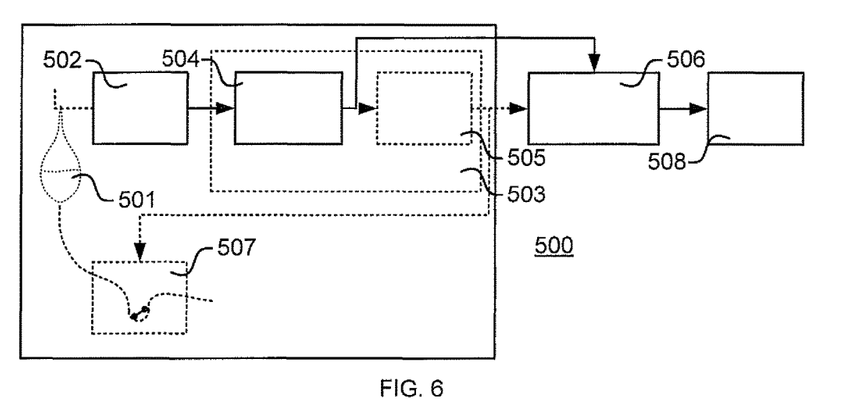
FIG. 6 schematically illustrates a medical apparatus according to an embodiment.

FIG. 6 schematically illustrates a medical apparatus 500 according to an embodiment. The medical apparatus 500 comprises a sensor 502 which provides an output signal to an adaptive filter 504 of the medical apparatus 500. The filtered signal from the adaptive filter 504 is provided to a state determiner 506 of the medical apparatus 500. The filtered signal may indicate a predicted error signal, i.e. a difference between a predicted estimate of the sensor signal and a value that the sensor would provide if a prescription was perfectly followed. The state determiner 506 is arranged to determine a state from the predicted error signal. Alternatively, the filtered sensor signal is provided indicating a predicted estimate of the sensor output, e.g. a measured weight, and the state determiner 506 is arranged to check this value against a desired value, e.g. according to the prescription, and provide the determined state therefrom. The determined state may be one of at least two non-critical states and a critical state, wherein the critical state may be an alarm state, i.e. an alarm is activated when the critical state occurs. The non-critical states may correspond to for example one state where everything in working within desired limits and another non-critical state is where some anomalies may be present, however not critical. The state determiner 506 provides the determined state to a user interface, UI, 508 of the medical apparatus 500, wherein the UI 508 indicates the state to an operator, e.g. the patient or medical staff. The indication may be performed by displaying an indication, e.g. through a screen or visual indicator of the UI 508. If the critical state occurs, both audio signal and visual indication may be provided, which is preferably performed according to alarm regulations associated with the type of medical apparatus. The displaying of the indication may for example comprise a thermometer or traffic light illustration of the determined state, or a meter indication. Examples for the provision of indication are discussed below. Different approaches, particularly for the non-critical states, may be provided to clearly indicate the state to the user. For example, the indication may comprise an indicator on how well the state of the operation of the medical apparatus corresponds to prescribed operation, or how much the state of the operation of the medical apparatus deviates from prescribed operation. That is, the indication can be considered from a positive side or a negative side, wherein the choice thereof may be made at design of the medical apparatus to correspond to other approaches used for the UI 508 such that the operator easily recognises the indications.

The sensor 502 may for example comprise scales arranged to measure weight of a container 501, e.g. a bag 5, 8, 11, 12, of a medical solution, e.g. dialysis fluid or some infusion fluid, and/or a flow sensor, as has been discussed above. The adaptive filter 504 may be a part of a controller 503 arranged to control fluid delivery to or from the container 501 by controlling e.g. a pump 507. The controller 503 may comprise some controlling arrangement, e.g. a PI controller 505, which receives the filtered signal from the adaptive filter 504 and performs the control based thereon. Here, the control signal that is the output of the control mechanism 505 may also or alternatively be provided to the state determiner 506, which may be arranged to determine the state thereon. The controlled amount may for example be flow, volume or mass to or from the container 501. The adaptive filter 504 may for example be a Kalman filter. Other filter solutions may be equally possible, such as other model predictive filters and observers. Here, it should be noted that e.g. in connection with predictive filters and the like, the term "state" is often used for internal values within the filter. This should not be confused with the state determined by the state determiner 506, and for the explanations of embodiments of the filter, the term "state" for internal values in the filters is avoided hereafter in this disclosure not to confuse.

Figure 7:
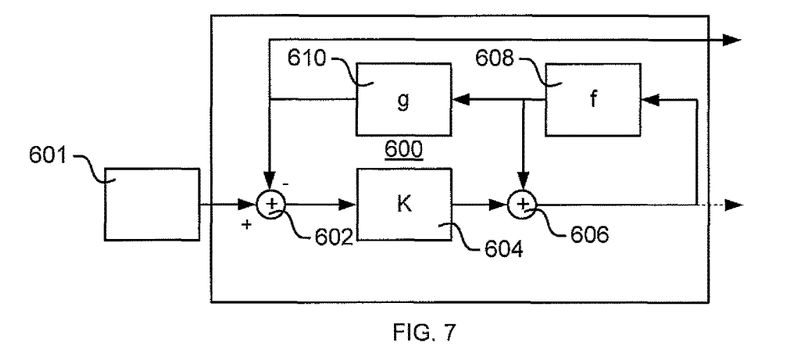
FIG. 7 is a schematic illustration of an adaptive filter and a sensor according to an embodiment.

FIG. 7 is a schematic illustration of an example of an adaptive filter 600 and a sensor 601 according to an embodiment. The output of the sensor 601 is provided to an input of the adaptive filter 600. The here described structure should be construed functionally, and the elements may not be considered as discrete element. The sensor signal is provided for a subtraction operation 602 where a predicted estimate is subtracted from the sensor signal to provide an innovation variable. The innovation variable is provided to a filter gain function 604 where it is multiplied with a filter gain, and the output of the filter gain function is provided for addition to a predicted estimate at an adding function 606 where it is added to form a corrected estimate. The corrected estimate is also provided to a prediction function 608, which outputs the predicted estimate. As demonstrated above, the predicted estimate is provided to the adding function 604, and it is also provided to a measurement prediction function 610 which provides the predicted estimate, which in turn is subtracted 602 from the next sample from the sensor 601. The predicted estimate from the measurement prediction function may be used as output of the filter. Alternatively or additionally, the corrected estimate may be provided as an output of the filter 600, and may for example be used for control operation. Here, there is a trade-off between timing constraints and precision, where the predicted estimate inherently has less lag while the corrected estimate inherently is more precise. For the determination of the state by the state determiner 506, at least the benefit of the less lag of the predicted estimate is used for enabling an early indication to the operator. The benefit of the more precise estimate by the corrected estimate may also be used by the state determiner 506 as an additional input for the determination. The prediction function 608 may also be called the system function and provides a model of the process the sensor is measuring. Thereby good predictions of values to be expected at the input may be made. The measurement prediction function 608 checks and updates the model, and provides for provision of a corrected estimate from the adding function 606.

The predicted estimate thus provides a value, which by the updating of the model fairly corresponds to the sample to be made, such that lag may be compensated for. Furthermore, the model provides for suppression of noise in the sampled signal. The predicted estimate, i.e. the output of the filter 504, 600, is compared with a value that should be expected at normal operation by the state determiner 506. Based on the deviation of the output of the filter from the expected normal value, the state determiner 506 is arranged to determine a state among a plurality of states. For example, the sensor comprises scales, and from the filtered sensor signal there may be determined a flow based on difference in weight measured by the scales. The deviation may be given from a set-point corresponding to the difference in weight measured by the scales and the corresponding filtered sensor signal. Based on the deviation, the state may be determined to be one of at least a non-critical states and a critical state, preferably at least two non-critical states such that one state corresponds to normal operation with no determined issues implying no actions to be taken to improve the situation, and another non-critical state with some issues, however non-critical, wherein an operator may improve the situation. The critical state requires actions, and also implies an alarm. Alternatively, the determined states by the determiner 506 may all be non-critical, although some state is such that a critical situation may be imminent, while the critical state is determined by a separate mechanism which also controls the alarm, i.e. a traditional alarm mechanism. The determiner 506 may use one or more thresholds for each state to which thresholds the deviation is compared with in order to determine the current state. The state is communicated to the operator by indications through the UI 508. Examples on such indications will be further elucidated below.

The filter may be arranged in a control mechanism of the apparatus, and may be implemented as software, e.g. run on a main processor of the apparatus. Considering the example with the four scales 110, 112, 114, 116 demonstrated with reference to FIGS. 1 and 2, each of these four scales may have a mechanism like the one demonstrated with reference to FIG. 6, i.e. four different states may be provided. These states are then indicated accordingly through the UI 508.

A benefit of at least some embodiments is that the operator proactively may keep the process such that alarms, and thus critical situations, may be avoided. Another benefit of at least some embodiments is that the operator may be better aware of the process through the information given by the indications of the states. Still another benefit of at least some embodiments is that if an alarm occurs, the operator may easier get an overview of the situation and may find a faster and/or more accurate way of dealing with the situation.

Figure 8:
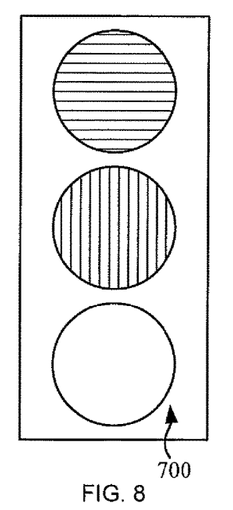
FIGS. 8 to 19 schematically illustrate approaches for providing indications through a user interface.

FIG. 8 schematically illustrates an approach for providing state indications 700 through the UI. A traffic light-resembling illustration indicates one of three states, e.g.: green (lower circle) for a non-critical state where the deviation is negligible, yellow (middle circle) for a non-critical state where deviation is such that an operator may improve the situation, and red (upper circle) for a critical state or a state where a critical state is imminent where the operator is required to take action. The critical state is in addition to the indication preferably also notified by an alarm according to conventional procedure, e.g. as prescribed by standards for the type of apparatus. Alternatively, the red state is a non-critical state indicating that actions by the operator are preferred to avoid a critical state, which is imminent. In this case, the alarm alone indicates the critical state. Other colours, and combinations of the indications, are also possible.

Figure 9:
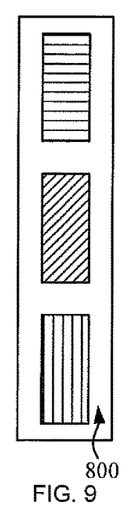

FIG. 9 schematically illustrates an approach for providing state indications 800 through the UI. The state indications 800 are similar to those demonstrated with reference to FIG. 8, but here has a slightly different visual approach. This visual approach may be beneficial over the approach demonstrated with reference to FIG. 8 when several state indicators 800 are to be fit in side-by-side on a user interface, where screen area normally is limited and other information also should fit in.

FIGS. 8 and 9 demonstrate illustration of distinct states. The state determiner is also preferred to make distinct state determinations. However, for some situations, the number of states may differ depending on e.g. operation mode, but the visual representation may be desired to be kept consistent. For such a situation, the indication 900 illustrated in FIG. 10 may be suitable where a bar indicates a level corresponding to the determined state. Thus, one of a number of states is indicated through the bar. Here, the approach for indication may either be chosen such that the optimal state is when the bar is full and the lower the bar is, the closer to a critical state, or be chosen such that the optimal state is when the bar is small and the higher the bar is, the closer to a critical state. Of these approaches, the chosen one is preferably such that the signal to the user is consistent, which preferably depends on the approach used for other indications in the UI.

Figure 10:
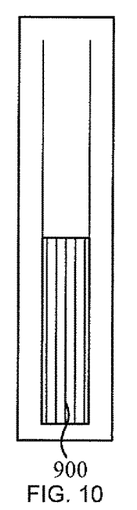
Figure 11:
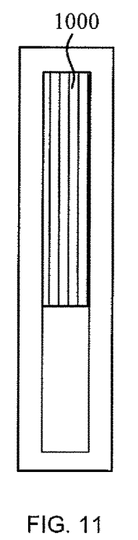

FIG. 11 illustrates an indicator 1000 similar to the one illustrated in FIG. 10, but where the bar grows from the top and downwards. In other senses, the alternatives demonstrated with reference to FIG. 10 apply also here.

Figure 12:
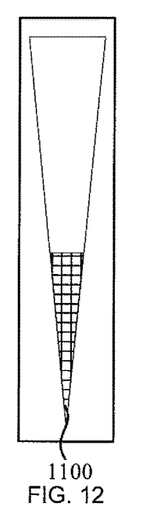

FIG. 12 illustrates an indicator 1100 based on the similar principle as the one in FIG. 10, but with the added feature that the width of the indicator 1100 is larger at one end. This is particularly beneficial when indications in the wide end corresponds to states closer to a critical state, wherein the visibility of the bar or level is increased for such states, particularly at some distance from a screen of the UI.

For the indicators 900, 1000, 1100 demonstrated with reference to FIGS. 10 to 12, a colour of different parts of the bar or the whole may be varied depending on the indicated state to further enhance perception by the user. The selection of colour scheme is preferably made according to the approach of other parts of the UI and/or according to any regulations for colour scheme in UI for the particular type of apparatus.

Figure 13:
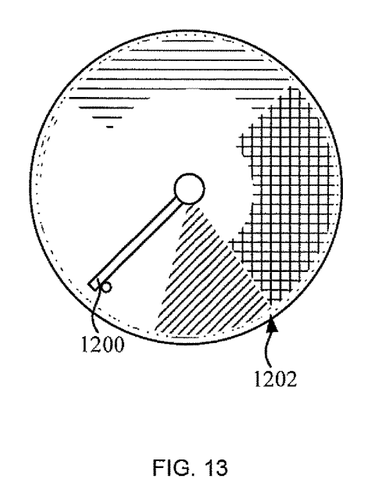

FIG. 13 illustrates a further approach for indicator 1200 where an illustration of an analogue meter is shown. The analogue meter may have indications 1202 on different states, e.g. by colour marking. In other senses, the analogue meter approach may be based on the similar principles as the indicators 900, 1000, 1100 demonstrated with reference to FIGS. 10 to 12.

Figure 14:
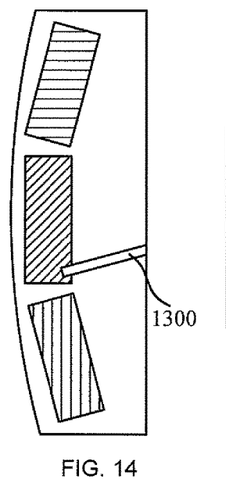

FIG. 14 illustrates another indicator 1300 based on an illustration of an analogue meter, and the similar principles as demonstrated above may be applied also for this indicator 1300.

Figure 15:
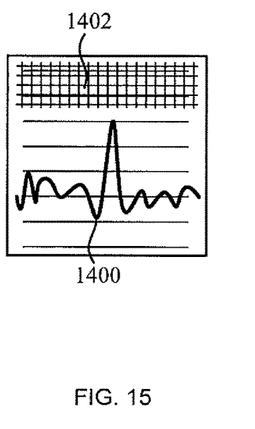

The filtering may, as demonstrated above, further comprise estimating a noise level of the sensor signal. The noise level may for example be estimated as a deviation based on the unfiltered signal and the filtered signal, e.g. observed in a time window. A noise level indicator may be included in the displayed indication. The noise level may be determined for one sensor, or may be based on observations of several sensors, e.g. on all the scales 110, 112, 114, 116 demonstrated with reference to FIGS. 1 and 2. When observing several sensors, the noise level may be correlated between the sensors, i.e. it may be expected that the noise is at least to some degree caused by external interference, e.g. mechanical phenomena affecting all the scales such as given by some examples above. An indication of noise level or noise level determined to be correlated between the plurality of sensors may be indicated, e.g. in connection with the indication as demonstrated with reference to any one of FIGS. 8 to 14. The indication on noise level may indicate, at least to some degree, the level for each sensor, or may indicate an overall determined noise level. FIG. 15 is an example on a noise indication 1400 where a noise level for each of a plurality of sensors is indicated and tied together as a single graph. The general level of the graph may then be interpreted by the operator as a general condition for all sensors, and the operator may also see that some of the sensors are affected to a higher or lower degree. For example, in the graph of FIG. 15 it can be seen that a sensor corresponding to the middle part of the graph is significantly more affected of noise than the others, and that for most of the sensors a general noise level is below an acceptable level (unacceptable levels indicated by shaded or coloured field 1402 in the upper part of the indication). The skilled operator may from the provided information make decisions and/or take actions which may safeguard patient safety or improve the situation.

Figure 16:
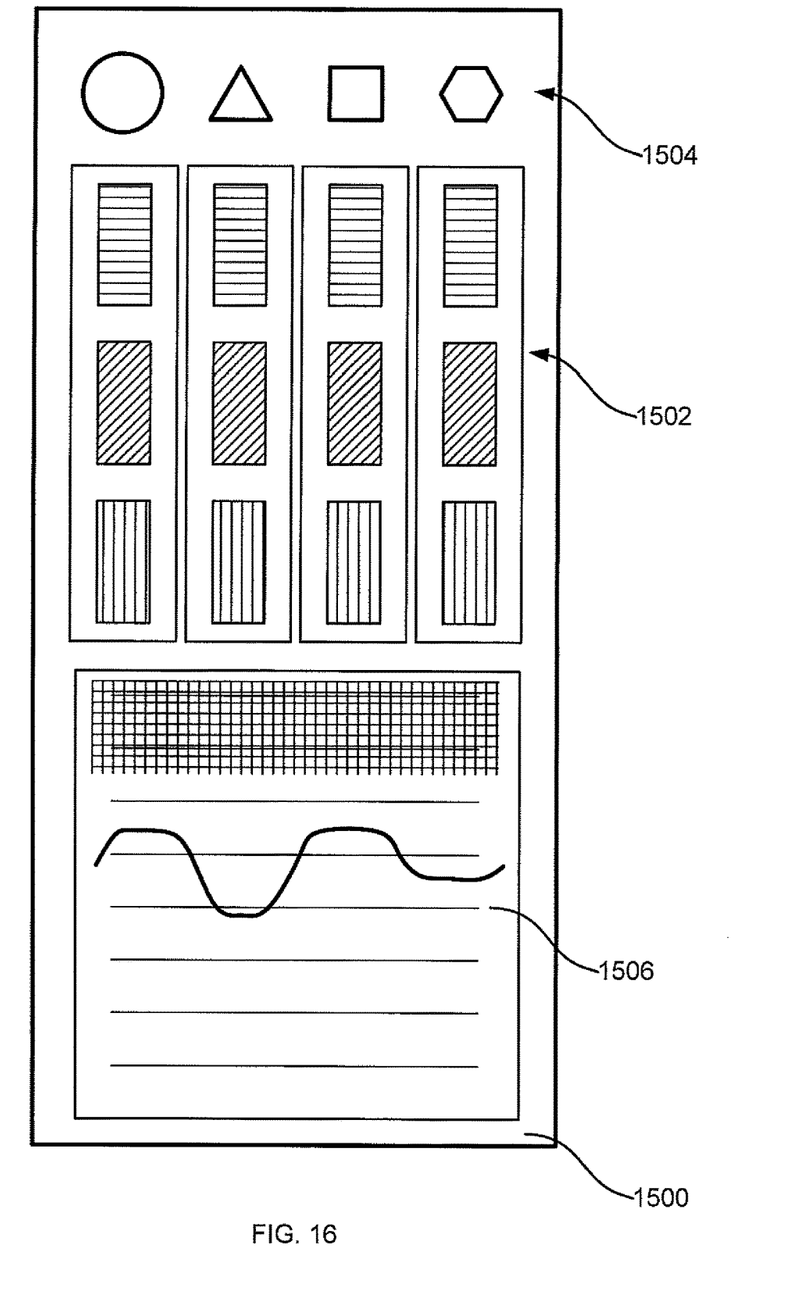

FIG. 16 illustrates an example of an aggregated indication 1500 for indicators 1502 for four sensors, e.g. the scales 110, 112, 114, 116 demonstrated with reference to FIGS. 1 and 2 above, wherein the symbols 1504 above the state indicators 1502 illustrates identification of the respective sensor or function associated to the sensor. Below the indicators 1502, a noise indicator diagram 1506 similar to the one demonstrated with reference to FIG. 15 is shown accordingly where the noise level for the respective sensor is shown accordingly.

In addition to the graphical indications demonstrated with reference to FIGS. 8 to 16 above, values may be presented by numbers in connection with the graphical indications.

Figure 17:
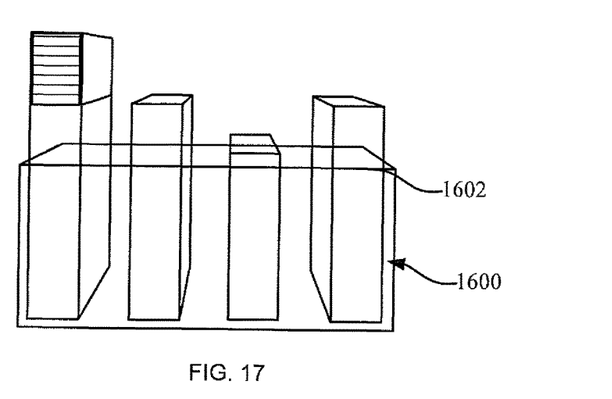
Figure 18:
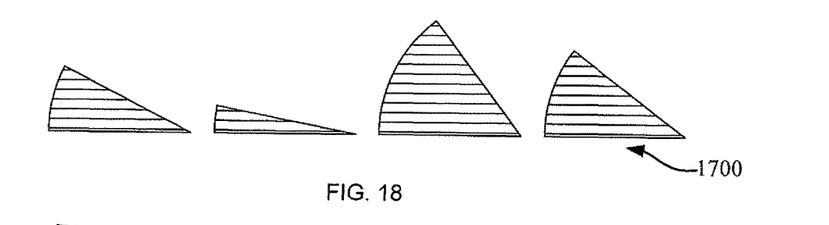
Figure 19:
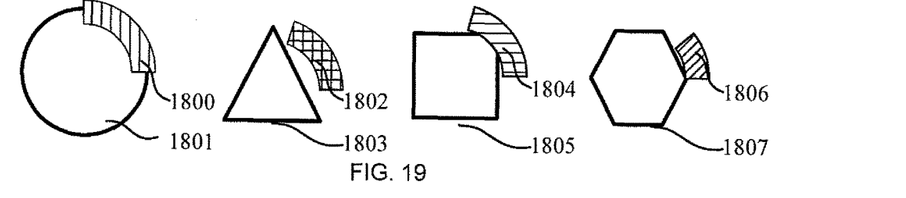

Further ways of presenting the indications are also possible, and will only be presented briefly below. FIG. 17 illustrates a combined illustration of the indicators 1600 and a common noise level 1602, where bars (similar to what is illustrated in FIG. 10) are growing upwards and the common noise level 1602 is indicated as a "noise floor". FIG. 18 illustrates indicators 1700 of "pie slice" type. FIG. 19 illustrates an indicator 1800, 1802, 1804, 1806 integrated with symbols 1801, 1803, 1805, 1807 indicating the identification of the respective sensor or function associated to the sensor. The indicators 1800, 1802, 1804, 1806 may also comprise dynamic behaviour, e.g. flashing or pulsating, for certain states, with or without combination with change in colour scheme etc. as demonstrated above.

The examples on presenting the indications set forth with reference to FIGS. 16 to 19 have been using four values, for easier understanding from the example of FIGS. 1 and 2, next to each other, which provides the benefit that a user may easily get an overview of the situation. Even with further values, this approach would still provide a fairly easy way for a user to understand the overall state, and to quickly identify what parts that may need some attention. The examples have been given with the indications side-by-side, but a presentation with the indications arranged vertically or horizontally is equally possible.

Figure 20:
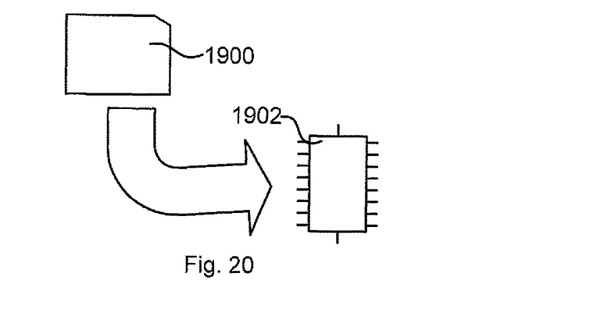
FIG. 20 schematically illustrates a computer readable medium and computer according to an embodiment

The methods according to the present invention are suitable for implementation with aid of processing means, such as computers and/or processors, especially for the case where the filtering is performed through software run on the processor of the medical apparatus. Therefore, there is provided computer programs, comprising instructions arranged to cause the processing means, processor, or computer to perform the steps of any of the methods and corresponding approaches for filtering and presentation of indicators according to any of the embodiments described with reference to FIGS. 3 and 7 to 19. The computer programs preferably comprise program code which is stored on a computer readable medium 1900, as illustrated in FIG. 20, which can be loaded and executed by a processing means, processor, or computer 1902 to cause it to perform the methods, respectively, according to embodiments of the present invention, preferably as any of the embodiments described with reference to FIGS. 3 and 7 to 19. The computer 1902 and computer program product 1900 can be arranged to execute the program code sequentially where actions of the any of the methods are performed stepwise, and/or in parallel, which is preferred for real-time performance where that is required or desired. The processing means, processor, or computer 1902 is preferably what normally is referred to as an embedded system. Thus, the depicted computer readable medium 1900 and computer 1902 in FIG. 20 should be construed to be for illustrative purposes only to provide understanding of the principle, and not to be construed as any direct illustration of the elements.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method of displaying a predicted state of a medical apparatus, the method comprising:
    receiving, continuously or repeatedly during operation of the medical apparatus, a sensor signal from a sensor of the medical apparatus;
    filtering the sensor signal by an adaptive filter such that a predicted signal is achieved;
    determining a state from the predicted signal; and
    displaying an indication of the predicted state of the medical apparatus through a user interface of the medical apparatus based on the determined state.

2. The method of claim 1, wherein the adaptive filter includes a Kalman filter.

3. The method of claim 1, wherein the filtering is performed by a controller in addition to the adaptive filter.

4. The method of claim 3, wherein the filtering, by the controller, further provides a signal for controlling a function of the medical apparatus being associated with the sensor.

5. The method of claim 1, wherein the sensor comprises a flow sensor, and the method comprises determining a flow by the flow sensor.

6. The method of claim 1, wherein the sensor comprises scales.

7. The method of claim 6, comprising determining a flow based on a difference in weight measured by the scales from the predicted signal.

8. The method of claim 5, comprising estimating an error based on a set-point corresponding to the determined flow, wherein the determining of the state is based on the estimated error.

9. The method of claim 1, wherein the state is one of at least two non-critical states or a critical state.

10. The method of claim 9, wherein an alarm is activated when the critical state occurs.

11. The method of claim 1, wherein the displaying of the indication comprises a thermometer or traffic light illustration of the determined state.

12. The method of claim 1, wherein the indication comprises a meter indication.

13. The method of claim 1, wherein the indication of the state comprises an indicator on at least one of
   how well the state of the operation of the medical apparatus corresponds to prescribed operation; and
   how much the state of the operation of the medical apparatus deviates from prescribed operation.

14. The method of claim 1, further comprising estimating, by the filtering, a noise level of the sensor signal, wherein the displaying of the indication comprises a noise level indicator.

15. The method of claim 1, wherein interactions with the medical apparatus known to introduce false error conditions are taken into account by the adaptive filter.

16. The method of claim 15, wherein the sensor comprises scales monitoring weight of a container holding medical fluid to be consumed during operation of the medical apparatus, and the interactions known to introduce false error conditions comprise replacing the container.

17. The method of claim 1, wherein a plurality of sensor signals are received and filtered, and respective states are determined, and wherein respective indications of the predicted states are displayed.

18. The method of claim 1, further comprising:
   receiving, continuously or repeatedly during operation of the medical apparatus, at least one further sensor signal from a further sensor of the medical apparatus;
   filtering the at least one further sensor signal by a respective adaptive filter such that respective predicted error signals are achieved;
   determining a respective state from the respective predicted error signal; and
   displaying a respective indication of the predicted state of the medical apparatus based on the respective determined state.

19. The method of claim 18, comprising:
   estimating an aggregate noise state based on the filtering of the respective sensor signals; and
   displaying an indicator of the aggregate noise state.

20. A medical apparatus comprising:
   a sensor arranged to provide a sensor signal, continuously or repeatedly during operation of the medical apparatus, for a function of the medical apparatus;
   an adaptive filter arranged to filter the sensor signal such that a predicted signal is achieved;
   a state determinator arranged to determine a state from the predicted signal; and
   a user interface arranged to display an indication based on the determined state.

21. The apparatus of claim 20, wherein the adaptive filter includes a Kalman filter.

22. The apparatus of claim 20, further comprising a controller arranged to provide a signal for controlling the function of the medical apparatus being associated with the sensor.

23. The apparatus of claim 20, wherein the sensor comprises a flow sensor arranged to determine a flow.

24. The apparatus of claim 20, wherein the sensor comprises scales.

25. The apparatus of claim 24, wherein the flow is determined based on a difference in weight measured by the scales from the predicted signal.

26. The apparatus of claim 23, arranged such that an error is estimated based on a set-point corresponding to the determined flow, wherein the state determinator is arranged to determine the state based on the estimated error.

27. The apparatus of claim 20, wherein the state is one of at least two non-critical states or a critical state.

28. The apparatus of claim 27, comprising an alarm mechanism which is activated when the critical state occurs.

29. The apparatus of claim 20, wherein the user interface is arranged to display the indication as a thermometer or traffic light illustration of the determined state.

30. The apparatus of claim 20, wherein the user interface is arranged to display the indication as a meter indication.

31. The apparatus of claim 20, wherein the indication of the state comprises an indicator on at least one of
   how well the state of the operation of the medical apparatus corresponds to prescribed operation; and
   how much the state of the operation of the medical apparatus deviates from prescribed operation.

32. The apparatus of claim 20, wherein the adaptive filter further is arranged to estimate a noise level of the sensor signal, and the user interface is arranged to display a noise level indicator.

33. A non-transitory computer readable medium, for a processor of a medical apparatus, comprising computer program code including computer executable instructions, which when downloaded and executed by the processor of the medical apparatus causes the medical apparatus to perform the method of claim 1.

* * * * *